(12) United States Patent
Wanda

(10) Patent No.: US 9,339,254 B2
(45) Date of Patent: May 17, 2016

(54) OBJECT INFORMATION ACQUIRING APPARATUS

(71) Applicant: CANON KABUSHIKI KAISHA, Tokyo (JP)

(72) Inventor: Koichiro Wanda, Yokohama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 156 days.

(21) Appl. No.: 14/150,897

(22) Filed: Jan. 9, 2014

(65) Prior Publication Data

US 2014/0196544 A1 Jul. 17, 2014

(30) Foreign Application Priority Data

Jan. 16, 2013 (JP) ................................. 2013-005534

(51) Int. Cl.
| | | |
|---|---|---|
| *A61B 5/1455* | (2006.01) | |
| *A61B 8/08* | (2006.01) | |
| *A61B 5/00* | (2006.01) | |
| *A61B 5/145* | (2006.01) | |

(52) U.S. Cl.
CPC ............. *A61B 8/0825* (2013.01); *A61B 5/0095* (2013.01); *A61B 5/14542* (2013.01); *A61B 5/4312* (2013.01); *A61B 8/483* (2013.01); *A61B 8/5261* (2013.01)

(58) Field of Classification Search
CPC .... A61B 5/0095; A61B 5/14551; A61B 5/72; A61B 5/7271
See application file for complete search history.

(56) References Cited

U.S. PATENT DOCUMENTS

| | | | | |
|---|---|---|---|---|
| 5,713,356 | A | * | 2/1998 | Kruger .......................... 600/407 |
| 5,840,023 | A | | 11/1998 | Oraevsky et al. ............. 600/407 |
| 6,846,288 | B2 | * | 1/2005 | Nagar et al. .................. 600/316 |
| 7,515,948 | B1 | * | 4/2009 | Balberg et al. ................ 600/323 |
| 7,864,307 | B2 | * | 1/2011 | Fukutani et al. ................ 356/73 |
| 8,991,261 | B2 | * | 3/2015 | Asao ............................... 73/655 |
| 2010/0087733 | A1 | * | 4/2010 | Nakajima et al. ............. 600/437 |
| 2012/0239318 | A1 | | 9/2012 | Tokita ............................ 702/56 |
| 2012/0289812 | A1 | | 11/2012 | Oishi ............................ 600/407 |

FOREIGN PATENT DOCUMENTS

| | | |
|---|---|---|
| JP | 2006-023820 | 1/2006 |
| JP | 2011-177496 | 9/2011 |
| WO | WO 2012/011242 | 1/2012 |
| WO | WO 2013/018285 | 2/2012 |

OTHER PUBLICATIONS

M. Xu et al., "Universal back-projection algorithm for photoacoustic computed tomography", *Physical Review E* 71, 016706 (Jan. 19, 2005).

* cited by examiner

*Primary Examiner* — Eric Winakur
(74) *Attorney, Agent, or Firm* — Fitzpatrick, Cella, Harper & Scinto

(57) ABSTRACT

An object information acquiring apparatus disclosed by this specification includes a detector configured to detect a photoacoustic wave generated from an object on which light is irradiated from a light source, a generator configured to generate, using the photoacoustic wave, an image indicating characteristic information in a photographing region in the object, an acquirer configured to acquire information concerning quantitativity of a measurement value of the photoacoustic wave in the photographing region, and an extractor configured to extract a region having quantitativity in the image on the basis of the information concerning quantitativity.

19 Claims, 11 Drawing Sheets

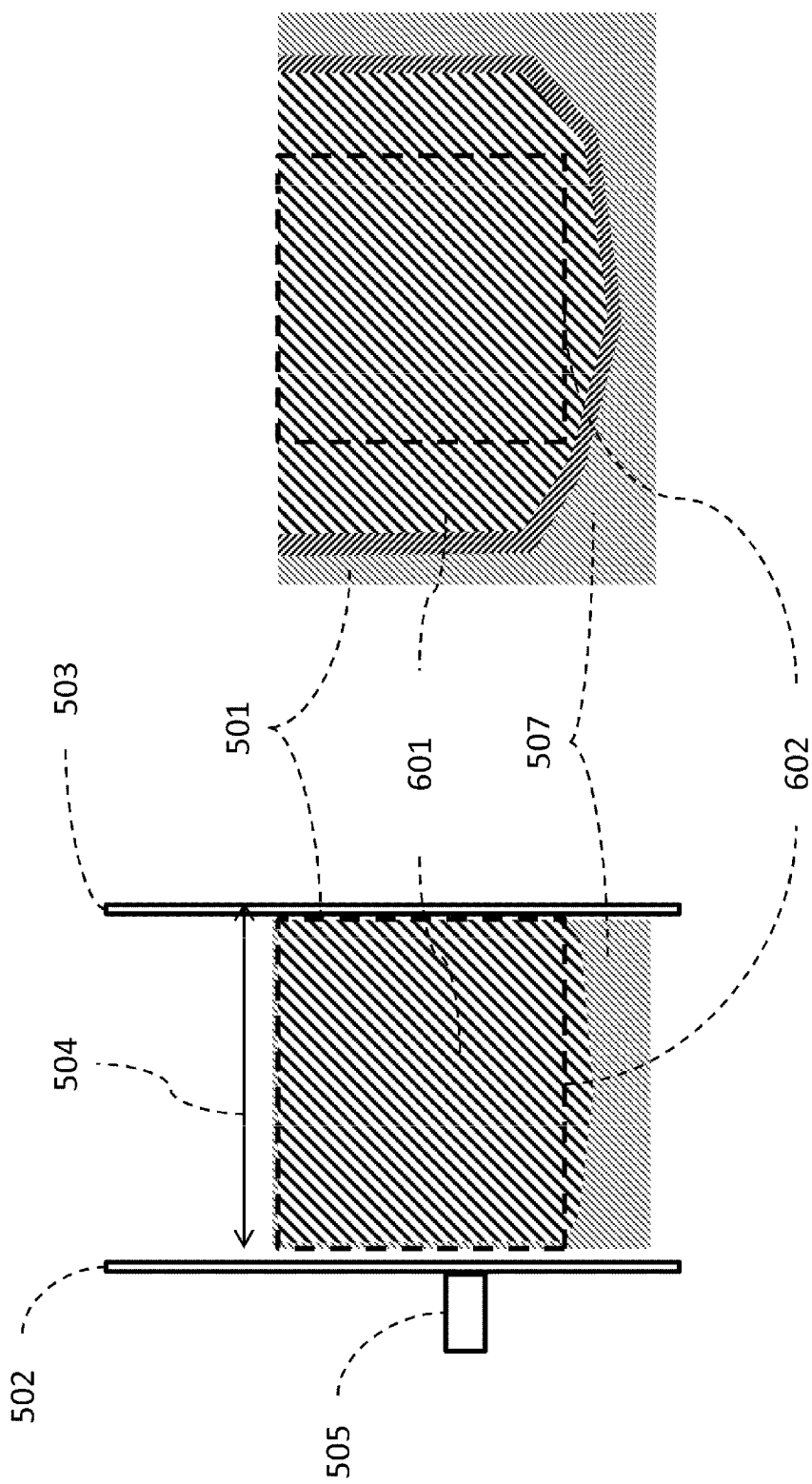

OBJECT INFORMATION ACQUIRING APPARATUS

BACKGROUND OF THE INVENTION

1. Field of the Invention

The present invention relates to an object information acquiring apparatus.

2. Description of the Related Art

A photoimaging apparatus for obtaining information concerning the inside of an object such as a living organism using light has been studied in the medical field. As one of such techniques, there is photoacoustic tomography (PAT). This is a technique for visualizing information related to an optical characteristic value inside an object on the basis of an acoustic wave generated from a biological tissue, which absorbs the energy of light propagated and diffused in the object. As an example of an information acquiring method, there is a method of detecting acoustic waves in a plurality of places surrounding an object and mathematically analyzing an obtained signal.

Information such as an initial sound pressure distribution and light energy absorption density obtained by the technique can be used for, for example, specifying a position of a malignant tumor involving multiplication of new born blood vessels. In the following explanation, description of the light energy absorption density distribution is omitted. However, the light energy absorption density distribution is considered to be the same as the initial sound pressure distribution. A visualized image (e.g., a three-dimensional reconstructed image) is useful for grasping the inside of a living organism in a medical diagnosis.

On the other hand, according to the progress of an information processing apparatus and the increase in a data capacity in recent years, a frequency of use of a three-dimensional medial image of a human body obtained by a CT or an MRI is increasing in a diagnosis in the medical field. In general, three-dimensional image data for a medical image diagnosis includes a form image and a function image. The form image indicates an image in which a characteristic of a form of an object is shown and that is excellent in display of anatomical information like a CT image. The function image is an image that is excellent in display of physiological information like a positron emission tomography (PET) image. An image obtained by the PAT is generally classified into the function image.

A photoacoustic effect and a characteristic of a reconstructed image in the PAT are explained. The photoacoustic effect is a phenomenon in which, when light such as pulse light is irradiated on an object, volume expansion occurs in a region with a high absorption coefficient and an acoustic wave (a compressional wave called photoacoustic wave; typically an ultrasound wave) is generated.

Theoretically, in the PAT, if a temporal change of the photoacoustic wave is measured by an ideal acoustic wave detector (wideband/dot detection) at various points of a closed space surface (in particular, a spherical measurement surface) surrounding the entire object, it is possible to completely visualize an initial sound pressure distribution caused by the light irradiation. It is know that, even if a space is not a closed space, if the temporal change can be measured in a columnar shape or a flat shape with respect to the object, it is possible to substantially reproduce the initial sound pressure distribution caused by light irradiation (see PHYSICAL REVIEW E 71, 016706(2005)).

The following Expression (1) is a partial differential equation called photoacoustic wave equation. If this expression is solved, it is possible to describe acoustic wave propagation from an initial sound pressure distribution and theoretically calculate in which place and how a photoacoustic wave can be detected.

[Math. 1]
$$\left(\nabla^2 - \frac{1}{c^2}\frac{\partial^2}{\partial t^2}\right)p(r, t) = -p_0(r)\frac{\partial \delta(t)}{\partial t} \quad (1)$$

where r represents position, t represents time, p(r, t) represents temporal change of sound pressure, $p_0(r)$ represents initial sound pressure distribution, c represents sound speed, and $\delta(t)$ represents delta function representing the shape of a light pulse.

On the other hand, the image reconstruction in the PAT is to derive the initial sound pressure distribution $p_0(r)$ from sound pressure $p_d(rd, t)$ obtained at a detection point and is mathematically called inverse problem. A universal back projection (UBP) method, which is a representative image reconstructing method, is explained. By analyzing the photoacoustic wave equation of Expression (1), it is possible to accurately solve the inverse problem for calculating $p_0(r)$. UBP is representation on a time domain of a result obtained by solving the inverse problem. Expression (2) is finally derived.

[Math. 2]
$$p_0(r) = -\frac{2}{\Omega_0}\nabla \cdot \int_{S_0} \vec{n}_0^S dS_0 \left[\frac{p_0(r_0, t)}{t}\right]_{t=|r-r_0|} \quad (2)$$

where $\Omega_0$ represents solid angle of an overall measurement area $S_0$ with respect to an arbitrary reconstruction voxel (or focus point).

When the expression is plainly transformed, the following Expression (3) is obtained:

[Math. 3]
$$p_0(r) = \int_{\Omega_0} b(r_0, t = |r - r_0|)\frac{d\Omega_0}{\Omega_0} \quad (3)$$

where $b(r_0, t)$ represents projection data and $d\Omega_0$ represents solid angle of a detector $dS_0$ with respect to an arbitrary observation point P. The initial sound pressure distribution $p_0(r)$ can be obtained by back-projecting the projection data according to the integral of Expression (3).

Note that $b(r_0, t)$ and $d\Omega_0$ are represented by the following Expressions (4) and (5):

[Math. 4]
$$b(r_0, t) = 2p(r_0, t) - 2t\frac{\partial p(r_0, t)}{\partial t} \quad (4)$$

$$d\Omega_0 = \frac{dS_0}{|r - r_0|^2}\cos\theta \quad (5)$$

where θ represents angle formed by the detector and the arbitrary observation point P.

When the distance between a sound source and a measurement position is sufficiently large compared with the size of the sound source (far sound field approximation), the following Expression (6) is obtained. In the expression, b(r₀, t) is represented by the following Expression (7):

[Math. 5]

$$p(r_0, t) \ll t \frac{\partial p(r_0, t)}{\partial t} \qquad (6)$$

$$b(r_0, t) = -2t \frac{\partial p(r_0, t)}{\partial t}. \qquad (7)$$

In this way, it is known that, in the image reconstruction of the PAT, the detection signal p(r₀, t) obtained by the detector is subjected to time derivative to obtain the projection data b(r₀, t) and the projection data b(r₀, t) is back-projected according to Expression (3) to calculate the initial sound pressure distribution p₀(r) (see PHYSICAL REVIEW E 71, 016706(2005))

However, Expression (1), which is the photoacoustic wave equation, used for calculating Expression (3) assumes "fixed sound speed", "measurement from all directions", "impulsive photoexcitation", "acoustic wave detection in a wideband", "acoustic wave detection at points", and "continuous sampling of acoustic waves". Realistically, it is not easy to realize an apparatus that satisfies these assumptions.

For example, realistically, it is difficult to detect an acoustic wave while surrounding an entire object. To increase a measurement area for an acoustic wave, it is necessary to increase the size of an acoustic wave detector and the number of elements and reinforce signal processing control. As a result, manufacturing costs increase. Because of such circumstances, a practical measurement apparatus often detects, from a specific direction, an acoustic wave from an object using a probe having a limited size.

As an example of the practical apparatus, an apparatus including a flat measurement system is devised (U.S. Pat. No. 5,840,023). The apparatus irradiates light on an object surrounded by flat plates, detects an acoustic wave with an acoustic wave detector arranged on the flat plate, and obtains a function image through image reconstruction. The apparatus can also calculate oxygen saturation on the basis of the detected acoustic wave. The oxygen saturation is content of oxygenated hemoglobin in total hemoglobin in blood. The oxygen saturation can be an index for determining whether the cardiopulmonary function is normally working and an index for determining malignity or benignancy of a tumor.

The calculation of oxygen saturation by the PAT is described in, for example, Japanese Patent Application Laid-open No. 2011-177496. Near infrared light is used for measurement of oxygen saturation. The near field light is easily transmitted through water constituting most of a living organism but is easily absorbed by hemoglobin in blood. Oxygenated hemoglobin and reduced hemoglobin respectively have different optical absorption spectra. Therefore, by irradiating the near infrared light on the living organism, it is possible to image a hemogram, which is form information of the living organism, and calculate an oxygen saturation value. Specifically, photoacoustic measurement is performed using near infrared light having different wavelengths and a comparison operation of a calculated optical absorption coefficient is performed. It is expected that diagnosis accuracy for breast cancer and the like is improved by displaying the calculated oxygen saturation value in addition to the image of the hemogram, which is the form information.

Patent Literature 1: U.S. Pat. No. 5,840,023
Patent Literature 2: Japanese Patent Application Laid-Open No. 2006-023820
Patent Literature 3: Japanese Patent Application Laid-open No. 2011-177496
Non Patent Literature 1: PHYSICAL REVIEW E 71, 016706 (2005)

SUMMARY OF THE INVENTION

However, a technique for enabling a user to identify differences in quantitativity in a reconstructed image and a three-dimensional image region of an oxygen saturation value has not been proposed. Therefore, when the oxygen saturation value is imaged, even the oxygen saturation value not having quantitativity is imaged.

This problem is specifically explained below. When an oxygen saturation value is calculated on the basis of data obtained by irradiating light having different wavelengths concerning a specific region of an object using a photoacoustic diagnostic apparatus, a distribution of oxygen saturation values is calculated concerning an entire measured three-dimensional image region.

For example, when a living organism such as a breast is photographed, an object is not always present in an entire photographing region. However, it is difficult to read information concerning a form of the object (e.g., presence or absence of the object) from an image of an oxygen saturation value, which is a function image. However, since the oxygen saturation value is calculated on the basis of a comparison operation of a light energy absorption density distribution of a plurality of wavelengths, even in a position outside the object, the oxygen saturation value is calculated. Therefore, a region where the quantitativity of the oxygen saturation value can be treated with reliability cannot be read in an oxygen saturation image, which is a function image.

Even information photographed in a position where the object is present is sometimes unsuitable for calculation of oxygen saturation. For example, when a breast is pressed by two holding plates to perform measurement, there are a three-dimensional region surrounded by a two-dimensional region where the object is in close contact with the holding plate and a region where the object floats from the holding plate.

In the former region where the breast is in close contact with the holding plates, conditions of light irradiation and acoustic wave measurement can be considered substantially fixed. However, in the latter region where the breast floats from the holding plate, conditions of light irradiation and acoustic wave measurement are different for each place and photographing with quantitativity cannot be performed. Therefore, when a non-contact region where the object floats is present in a photographing region, quantitativity is lost in a measured value. Therefore, even if it is attempted to perform, concerning the photographing region, a diagnosis making use of an imaged oxygen saturation value together with form information, an oxygen saturation value is calculated and displayed irrespective of presence or absence of quantitativity. Therefore, it is difficult to identify a region effective for the diagnosis.

In general, to accurately identify an accurate shape of a breast in a state pressed by the holding plates, it is necessary to add an expensive sensor and a complicated component. Therefore, manufacturing costs of an apparatus and labor and time are increased. When an object is a pressed breast, even if the object is present in the photographing region, oxygen saturation does not always have quantitativity.

Therefore, it is a problem of the present invention to make it possible to identify a region of a calculated oxygen saturation value having quantitativity when an oxygen saturation image is generated using a three-dimensional image photographed by a photoacoustic diagnostic apparatus.

The present invention has been devised in view of the problem and it is an object of the present invention to make it possible to identify a region having quantitativity in an image obtained by photoacoustic tomography.

The present invention provides an object information acquiring apparatus comprising:

a detector configured to detect a photoacoustic wave generated from an object on which light is irradiated from a light source;

a generator configured to generate, using the photoacoustic wave, an image indicating characteristic information in a photographing region in the object;

an acquirer configured to acquire information concerning quantitativity of a measurement value of the photoacoustic wave in the photographing region; and an extractor configured to extract a region having quantitativity in the image on the basis of the information concerning quantitativity.

According to the present invention, it is possible to identify a region having quantitativity in an image obtained by photoacoustic tomography.

Further features of the present invention will become apparent from the following description of exemplary embodiments with reference to the attached drawings.

BRIEF DESCRIPTION OF THE DRAWINGS

FIGS. 6A and 6B are diagrams showing a relation between the object and the photographing region;

DESCRIPTION OF THE EMBODIMENTS

Figure 1:
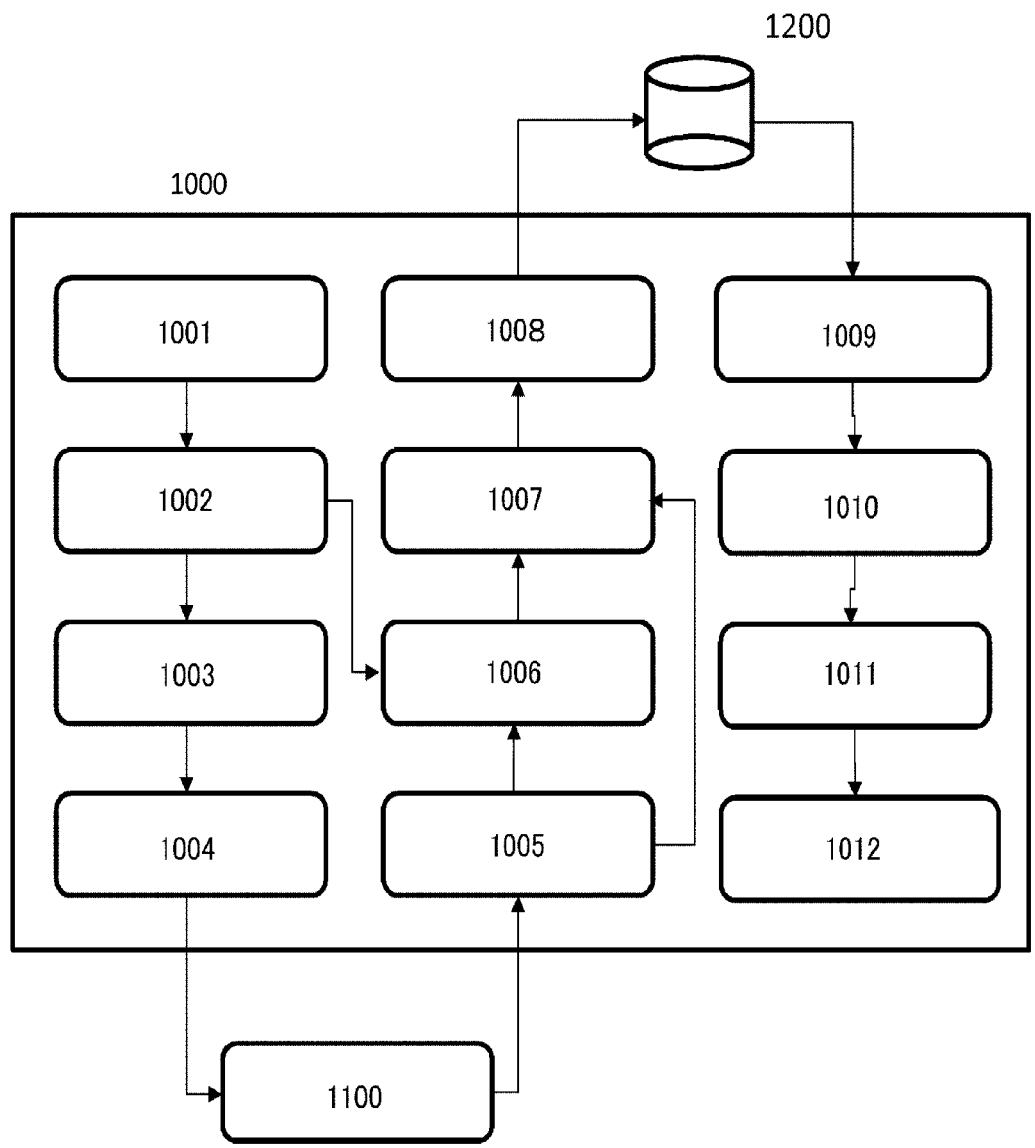
FIG. 1 is a diagram showing functional blocks of a photoacoustic diagnostic apparatus.

Preferred embodiments of the present invention are explained below with reference to the drawings. However, dimensions, materials, shapes, a relative arrangement, and the like of components described blow should be changed as appropriate according to the configuration of an apparatus applied with the invention and various conditions and are not meant to limit the scope of the present invention to the following description.

In the present invention, an acoustic wave includes elastic waves called a sound wave, an ultrasound wave, a photoacoustic wave, and a photo ultrasound wave. An object information acquiring apparatus of the present invention is an apparatus that irradiates light (an electromagnetic wave) on an object to thereby receive an acoustic wave generated in the object and acquires characteristic information in the object making use of a photoacoustic effect.

Object information in the object information acquiring apparatus is characteristic information that reflects initial sound pressure of an acoustic wave generated by light irradiation or light energy absorption density and an absorption coefficient derived from the initial sound pressure or concentration of a substance forming a tissue. The concentration of the substance is, for example, concentration of oxygenated hemoglobin and reduced hemoglobin and oxygen saturation. The characteristic information may be distribution information of positions in the object rather than numerical value data. That is, an initial sound pressure distribution, an absorption coefficient distribution, an oxygen saturation distribution, or the like may be generated as image data.

The present invention can also be grasped as a control method used when an acoustic wave is received by such an object information acquiring apparatus. In the embodiments explained below, a photoacoustic diagnostic apparatus is explained as a specific example of the object information acquiring apparatus.

First Embodiment

A photoacoustic diagnostic apparatus according to a first embodiment extracts a quantitative region in a photographed three-dimensional image region from information concerning a close contact region of an object and a holding plate and a result of threshold processing for a photoacoustic wave signal.

In this embodiment, a boundary surface of a region where the object is in close contact with the holding plate is calculated. The region is a range in which an acoustic wave detector scanning on the holding plate can correctly measure a photoacoustic wave. A light irradiation region on the object obtained by connecting a region irradiated through the holding plate in one photographing to the object in close contact with a pressing plate on a light projection side is calculated. A region where three-dimensional regions obtained by moving the respective regions in parallel to the boundary surface of the holding plate and the object opposed to each other overlap is set as a region having quantitativity.

Functional Block Diagram

Figure 2:
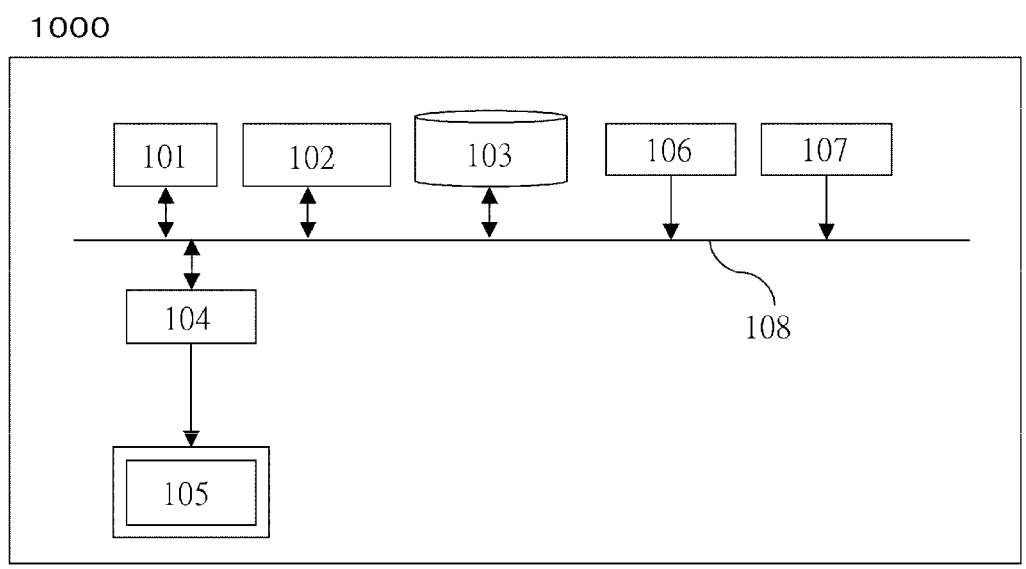
FIG. 2 is a diagram showing a configuration example of an information processing unit.
Figure 3:
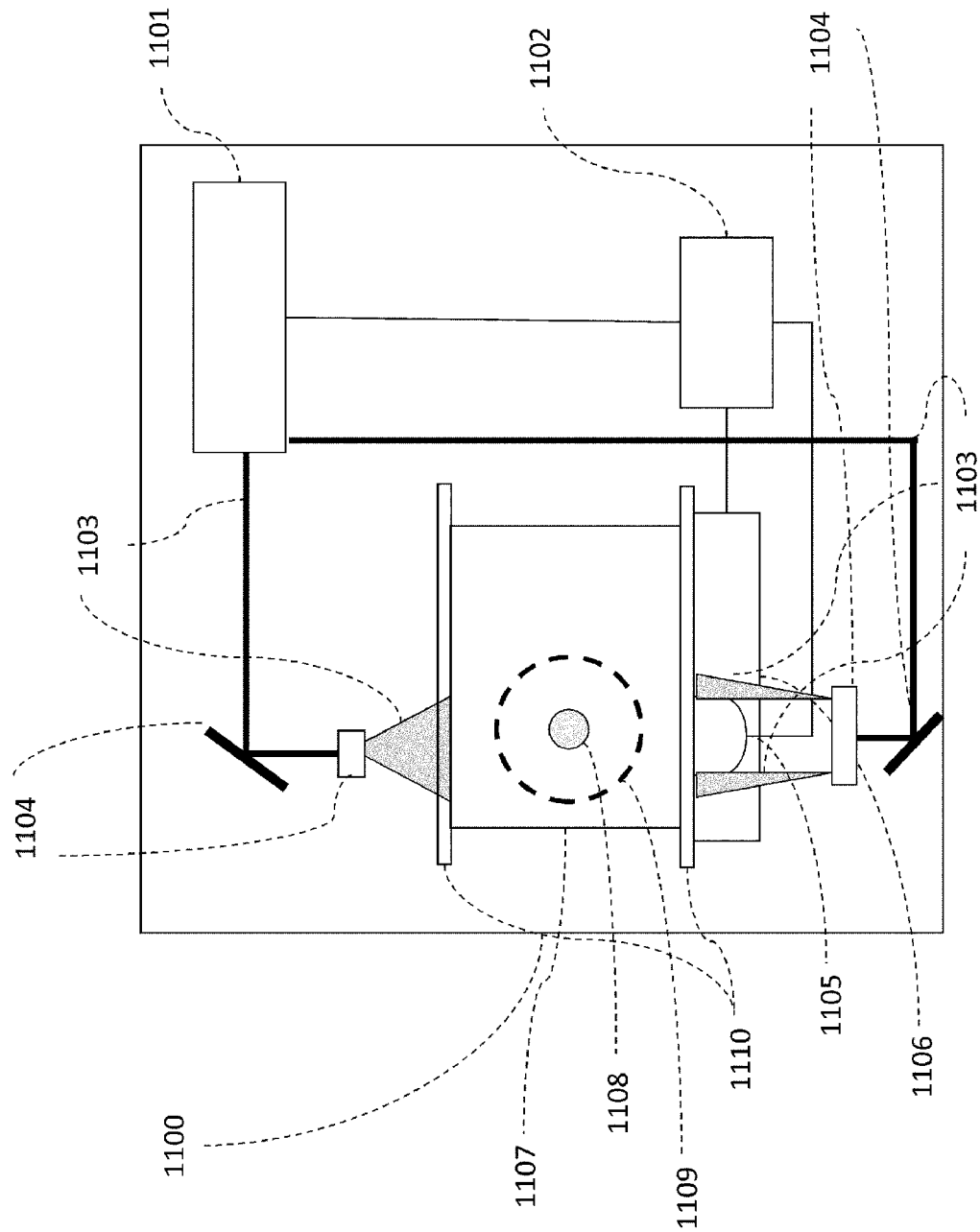
FIG. 3 is a diagram showing a configuration example of a photoacoustic wave signal measuring unit.

FIG. 1 shows a functional configuration of the photoacoustic diagnostic apparatus according to this embodiment. The photoacoustic diagnostic apparatus includes an information processing unit 1000 and a photoacoustic wave signal measuring unit 1100. FIG. 2 is an example of the configuration of the information processing unit 1000 of the photoacoustic diagnostic apparatus according to this embodiment. FIG. 3 is an example of the configuration of the photoacoustic wave signal measuring unit 1100.

The photoacoustic wave signal measuring unit 1100 performs measurement based on a photoacoustic wave measuring method instructed by the information processing unit 1000 and transmits photoacoustic wave signal information to the information processing unit 1000.

An acoustic wave detector 1105 is, for example, an ultrasonic probe. The photoacoustic wave signal information is information of a receiving element such as information concerning a photoacoustic wave signal detected by an element of a probe and a measurement value of the photoacoustic wave signal and the position, the sensitivity, and the directivity of an element arranged on a reception surface of the acoustic wave detector 1105. The photoacoustic wave signal information also includes information concerning conditions during photoacoustic wave signal acquisition such as photographing parameters of photoacoustic wave acquisition and other measurement information. The acoustic wave detector 1105 is equivalent to a detector of the present invention.

When the photoacoustic wave signal measuring unit 1100 moves the probe and detects an acoustic wave, a scanning region where the probe detects the acoustic wave is treated as a reception region and the position of the element that detects the acoustic wave is treated as an element position on the reception region. In this case, the photoacoustic wave signal information also includes the position of the reception region in a coordinate system inside the apparatus and the element position on the reception region. Further, control information of a light source and information concerning a pressing state of an object are also included in the photoacoustic wave signal information as conditions during photoacoustic wave signal acquisition.

Among these kinds of photoacoustic wave signal information, concerning the photoacoustic wave signal, an obtained signal itself may be transmitted or the obtained signal may be transmitted after being subjected to element sensitivity correction or gain correction. Signal acquisition may be repeated a plurality of times in the same position on the object and an average of measurement values may be transmitted. The same element of the probe does not always have to perform the photoacoustic wave detection a plurality of times. That is, an average may be calculated from a group of signals detected by elements having the same ability in the same position on the reception region.

A value, which may be a static constant, among the kinds of photoacoustic wave signal information may be stored in the information processing unit 1000 in advance and used for image reconstruction processing. On the other hand, dynamically set information is transmitted from the photoacoustic wave signal measuring unit 1100 to the information processing unit 1000 every time photographing is performed. As an example, information concerning the position of the element on the reception surface of the acoustic wave detector 1105 is explained. After position information of an identifier of the element and a probe is transmitted from the photoacoustic wave signal measuring unit 1100 to the information processing unit 1000, image reconstruction is performed with reference to relative position information of the probe and the element stored in the information processing unit 1000 in advance.

The information processing unit 1000 acquires an instruction concerning photographing from a user, determines a photoacoustic wave measuring method taking into account the quality of a reconstructed image, and transmits the photoacoustic wave measuring method to the photoacoustic wave signal measuring unit 1100. The information processing unit 1000 performs three-dimensional image reconstruction processing using photoacoustic wave signal information obtained from the photoacoustic wave signal measuring unit 1100 and displays data.

Functional blocks of the information processing unit 1000 are explained. The information processing unit 1000 includes a photographing instruction information acquiring unit 1001, a reconstruction method determining unit 1002, a photoacoustic wave measuring method determining unit 1003, a photoacoustic wave measuring method instructing unit 1004, a photoacoustic wave signal information acquiring unit 1005, a reconstruction processing unit 1006, and a quantitative region extracting unit 1007. The information processing unit 1000 further includes a data recording unit 1008, a data acquiring unit 1009, a data analyzing unit 1010, a display information generating unit 1011, and a display unit 1012.

The photographing instruction information acquiring unit 1001 acquires, as photographing instruction information, an instruction concerning photographing input from the user via an input unit 106. As examples of the instruction concerning photographing, there are, for example, information concerning a photographing region designating a region that should be photographed in the apparatus by the photoacoustic wave signal measuring unit 1100 and information for specifying the quality of a reconstructed image.

Designation of the photographing region only has to be a method that can specify a three-dimensional region. For example, there is a method of designating only a two-dimensional region on the holding plate and setting, as a photographing region, a rectangular parallelepiped having the two-dimensional region as one surface and having the thickness of the object as depth. There is also a method of setting, as preset information, a region specified in a coordinate system in the apparatus and designating an identifier of the region.

As an example of the information for specifying the quality of the reconstructed image, there is the number of photoacoustic wave signals used for reconstruction processing. Specifically, the number of photoacoustic wave signals used at points in the reconstruction region and relative detection positions with respect to the points of a photoacoustic signal necessary for the points are designated. Conditions may be set on the basis of a range of directivity of the element of the probe.

It is possible to limit the size and the bias of an artifact according to such conditions concerning the photoacoustic wave signal. Further, it is possible to set parameters corresponding to characteristics of a reconstruction algorism and add acoustic characteristics and reception conditions of an environment in which a photoacoustic wave is detected. As an input by the user, an input method for selecting an image quality level with these conditions preset may be used.

The photographing instruction information acquiring unit 1001 acquires instruction information concerning photographing and transmits the instruction information to the reconstruction method determining unit 1002. The photographing instruction information may include information used in analysis processing after photographing (e.g., a record of a region having quantitativity) besides setting concerning a photographing function. For example, the photographing instruction information includes setting concerning information extraction (presence or absence of extraction, a type of an extracting method, etc.) concerning a region having quantitativity for treating analysis data later such as oxygen saturation.

The reconstruction method determining unit 1002 determines, on the basis of the photographing instruction information, a reconstruction method to satisfy the set conditions and generates the reconstruction method as reconstruction instruction information. In generating the reconstruction instruction information, the ability of the photoacoustic wave signal measuring unit 1100 and the processing ability of the reconstruction processing unit 1006 are taken into account. As the reconstruction instruction information, there are reconstruction region information corresponding to a photographing region, a reconstruction algorithm, and information such as parameters of reconstruction processing such as the number of voxels to be reconstructed and a pitch. When the reconstruction processing cannot be carried out in the same processing because of a factor such as a measurement environment in the photographing region, a method of dividing the photographing region into a plurality of reconstruction regions and generating reconstruction instruction information of the respective regions may be adopted.

The reconstruction method determining unit 1002 transmits the generated reconstruction instruction information to the reconstruction processing unit 1006. The reconstruction method determining unit 1002 transmits both of the reconstruction instruction information and the photographing instruction information to the photoacoustic wave measuring method determining unit 1003. However, concerning the photographing instruction information, the photographing instruction information acquiring unit 1001 may directly transmit the photographing instruction information to the photoacoustic wave measuring method determining unit 1003.

The photoacoustic wave measuring method determining unit 1003 determines a photoacoustic wave measuring method of the photoacoustic wave signal measuring unit 1100 on the basis of the acquired reconstruction instruction information and photographing instruction information. As contents to be determined, there are, for example, a light source, an optical path, and the like concerning irradiation light and setting information related to irradiation light control. The photoacoustic wave measuring method determining unit 1003 also determines setting concerning photoacoustic wave reception such as a scanning region of the probe. The photoacoustic wave measuring method determining unit 1003 calculates, on the basis of the information concerning the photographing region in the photographing instruction information and reconstruction method information in the reconstruction instruction information, a scanning region necessary for carrying out the designated reconstructing method at respective points of the reconstruction region.

In a probe of a general linear system that transmits and receives an ultrasound wave, a surface of a rectangular parallelepiped region set as a photographing target is often set as a scanning region. However, in the photoacoustic wave diagnostic apparatus, a scanning region does not always coincide with a surface of a rectangular parallelepiped region set as a photographing target.

The photoacoustic wave measuring method determining unit 1003 also determines an element position and a pitch on the reception region necessary for satisfying the setting conditions of the reconstruction instruction information. The photoacoustic wave signal measuring unit 1100 basically carries out, for example, a correction method based on parameters in apparatus control for detecting an acoustic wave and acoustic characteristics in the apparatus. However, conditions such as parameters and a correction method concerning photoacoustic wave acquisition conditions related the image quality of the reconstruction processing may be determined by the photoacoustic wave measuring method determining unit 1003.

The photoacoustic wave measuring method determining unit 1003 creates, on the basis of these conditions, photoacoustic wave measurement information obtained by collecting instruction information necessary for measurement in the photoacoustic wave signal measuring unit 1100 and transmits the photoacoustic wave measurement information to the photoacoustic wave measuring method instructing unit 1004. The photoacoustic wave measurement information is created every time photographing is performed. However, a method of creating a plurality of kinds of photoacoustic wave measurement information in advance and designating photoacoustic wave measurement information with an identifier or the like may be adopted. The photoacoustic wave measuring method instructing unit 1004 transmits the photoacoustic wave measurement information to the photoacoustic wave signal measuring unit 1100 and instructs photoacoustic wave measurement.

The photoacoustic wave signal information acquiring unit 1005 transmits the photoacoustic wave signal information, which is transmitted from the photoacoustic wave signal measuring unit 1100, to the reconstruction processing unit 1006. The photoacoustic wave signal information acquiring unit 1005 extracts, from the photoacoustic wave signal information, information for quantitative region calculation, which is information for calculating a quantitative region in the photographing region and transmits the information for quantitative region calculation to the quantitative region extracting unit 1007. The photoacoustic wave signal information acquiring unit 1005 is equivalent to an acquirer of the present invention.

The reconstruction processing unit 1006 performs, for each of points in a region for performing image reconstruction, three-dimensional image reconstruction using only a selected photoacoustic wave signal and generates a three-dimensional reconstructed image (volume data). This reconstruction processing is performed on the basis of the reconstruction instruction information sent from the reconstruction method determining unit 1002 and the photoacoustic wave signal information sent from the photoacoustic wave signal information acquiring unit 1005. The reconstruction processing unit 1006 transmits the generated reconstructed image and the information for quantitative region calculation to the quantitative region extracting unit 1007. The reconstruction processing unit 1006 is equivalent to a generator of the present invention.

As a method of the image reconstruction processing, three-dimensional image reconstruction by an analysis such as a time domain method or a Fourier domain method can be used. The reconstruction processing unit 1006 may generate any of reconstructed images indicating an initial sound pressure distribution, a light absorption coefficient distribution, and a distribution of oxygen saturation values. The reconstruction processing unit 1006 may superimpose a result of other analysis processing on these images. Further, the reconstruction processing unit 1006 may perform various kinds of image correction such as correction for non-uniformity of light intensity. When some change or correction is necessary for the reconstruction region or the reconstruction parameters because a part of photoacoustic wave measurement fails in the photoacoustic wave signal measuring unit 1100, the change or the correction can be carried out together with the reconstruction.

The quantitative region extracting unit 1007 generates recording data on the basis of the reconstructed image sent from the reconstruction processing unit 1006 and the information concerning light irradiation concerning the photographing region acquired from the photoacoustic wave signal information acquiring unit 1005. The recording data to be generated is generated as, with addition of the information concerning light irradiation, for example, volume data for each of voxels formed by dividing the photographing region at a predetermined pitch. The quantitative region extracting unit 1007 transmits the generated recording data to the data recording unit 1008. The quantitative region extracting unit 1007 is equivalent to an extractor of the present invention.

As an example of a data format, a digital imaging and communications in medicine (DICOM) format, which is a standard specification of a medical image, can be used. By storing information concerning light irradiation in a private tag in the format, it is possible to add information concerning light irradiation while maintaining versatility of volume data. This recording data can be analyzed and displayed together with the information concerning the light irradiation using a viewer corresponding to a DICOM Image.

The data recording unit 1008 stores the recording data generated by the quantitative region extracting unit 1007 in a storage medium such as a magnetic disk 103 as a recording data file 1200. A recording destination is not limited to the magnetic disk 103. The recording data may be stored in, for example, another information processing apparatus through a network. The data recording unit 1008 is equivalent to a recording unit of the present invention.

The data acquiring unit 1009 acquires the recording data from the recording data file 1200 and transmits the recording data to the data analyzing unit 1010.

The data analyzing unit 1010 analyzes the format of the recording data acquired from the data acquiring unit 1009 and extracts the reconstructed image generated by the reconstruction processing unit 1006 and the information concerning the light irradiation acquired from the photoacoustic wave signal measuring unit 1100 by the photoacoustic wave signal information acquiring unit 1005. The data analyzing unit 1010 transmits the extracted reconstructed image and information concerning the light irradiation to the display information generating unit 1011.

The display information generating unit 1011 generates display information based on the reconstructed image and the information concerning the region having quantitativity. If the reconstructed image is a plane image that can be displayed in a range of a brightness value of a display, the reconstructed image is used as it is. If the reconstructed image exceeds the range of the display brightness value, appropriate conversion processing is performed. When the reconstructed image is a three-dimensional image such as volume data, an arbitrary method such as volume rendering, multiplanar reformation, or maximum intensity projection is used. Other information may be integrated in the display information as long as the reconstructed image can be displayed. The display information generating unit 1011 transmits the display information to the display unit 1012.

As examples of the display information based on the information having quantitativity, there are, for example, a boundary line that can identify the region having quantitativity and a display color different for each of regions indicating presence or absence of quantitativity. An annotation such as text information indicating a measurement value of the region having quantitativity and characteristics of the region, an analysis result, and the like can be added.

The display unit 1012 is a graphic card for displaying generated display information or a display device such as a liquid crystal or CRT display. The display unit 1012 displays the display information sent from the display information generating unit 1011.

The photoacoustic wave signal measuring unit 1100 and the information processing unit 1000 are separately explained. Specifically, an apparatus configuration of a measuring apparatus such as a digital mammography and a control apparatus (or a PC) is an example. However, the photoacoustic wave signal measuring unit 1100 and the information processing unit 1000 may be included in one apparatus. A general ultrasonic diagnosis apparatus may include both functions equivalent to the photoacoustic wave signal measuring unit 1100 and the information processing unit 1000 of the present invention.

The information processing unit 1000 may be divided into two kinds of configurations, i.e., a configuration for generating recording data from photoacoustic wave signal information at time different from photographing time and a configuration for performing only display from the recording data. An apparatus specialized for a recording function of the information processing unit 1000 is an apparatus including only the photoacoustic wave signal information acquiring unit 1005, the reconstruction processing unit 1006, the quantitative region extracting unit 1007, and the data recording unit 1008. An apparatus specialized for a display function of the information processing unit 1000 is an apparatus including the data acquiring unit 1009, the data analyzing unit 1010, the display information generating unit 1011, and the display unit 1012. The effects of the present invention can also be obtained by the apparatus specialized for the display function that uses information concerning the region having quantitativity in this way.

FIG. 2 is a diagram showing a basic configuration of a computer for realizing, with software, functions of units of the information processing unit 1000.

A CPU 101 controls the operations of components of the information processing unit 1000. A main memory 102 stores a control program executed by the CPU 101 and provides a work area during the program execution by the CPU 101. The magnetic disk 103 stores, for example, an operating system, a device driver of a peripheral device, and various kinds of application software including a program for performing, for example, processing of flowcharts explained below. A display memory 104 temporarily stores data for display for a monitor 105.

The monitor 105 is, for example, a CRT display or a liquid crystal monitor. The monitor 105 displays an image on the basis of data from the display memory 104. The input unit 106 is a unit with which an operator performs a pointing input, a character input, and the like such as a mouse and a keyboard. Operation by the operator in the embodiment of the present invention is performed through the input unit 106. The monitor 105 is equivalent to a display unit of the present invention.

An I/F 107 performs exchange of various data between the information processing unit 1000 and the outside. The I/F 107 is configured by IEEE1394, a USB, an Ethernet port (registered trademark), or the like. Data acquired via the I/F 107 is captured into the main memory 102. The components are connected by a common bus 108 to be capable of communicating with one another.

FIG. 3 is a diagram showing a photoacoustic diagnostic apparatus, which is an example of the configuration of the photoacoustic wave signal measuring unit 1100. A light source 1101 is a light source such as a laser or a light emitting diode that irradiates light on an object. As the irradiation light, light having a wavelength that is absorbed by a specific component included in the object at a high degree of absorption is used.

The control unit 1102 controls the light source 1101, an optical device 1104, the acoustic wave detector 1105, and position control means 1106. The control unit 1102 amplifies an electric signal detected by the acoustic wave detector 1105 and converts the electric signal from an analog signal into a digital signal. The control unit 1102 performs various kinds of signal processing and correction processing. The control unit 1102 transmits a photoacoustic wave signal from the photoacoustic wave signal measuring unit 1100 to an external device such as the information processing unit 1000 via a not-shown interface. As content of control of a laser, there is control of timing, a waveform, intensity, and the like of laser irradiation. Concerning the position control means 1106 of the acoustic wave detector 1105, the control unit 1102 performs movement control to an appropriate position. The control unit 1102 performs synchronization control of timings of laser irradiation and photoacoustic wave measurement. Further, the control unit 1102 performs signal processing for calculating an average from a photoacoustic wave signal for each of elements in a plurality of times of photoacoustic measurement.

The optical device 1104 is, for example, a mirror that reflects light or a lens that collects and expands light and changes the shape of the light. A light guide such as an optical fiber can also be used. Any device may be used as the optical device 1104 as long as light 1103 emitted from the light source is irradiated on an object 1107 in a desired shape. It is also possible to arrange a plurality of the light sources 1101 and a plurality of the optical devices 1104 and irradiate light on the photographing region from various directions. When the light is irradiated on the photographing region, the light may be irradiated on the object from one side or may be irradiated from both sides. When light is irradiated on the object 1107 from the light source 1101 under the control by the control unit 1102, a photoacoustic wave 1109 is emitted from a light absorber 1108 (equivalent to a sound source).

As the acoustic wave detector 1105, an acoustic wave detector such as a transducer that makes use of a piezoelectric phenomenon, a transducer that makes use of resonance of light, or a transducer that makes use of a change in a capacity may be used. The acoustic wave detector 1105 may directly come into contact with the object 1107 and detect an acoustic wave or may detect the acoustic wave through the holding plate that presses the object.

In the acoustic wave detector in this embodiment, a plurality of elements are two-dimensionally arranged. Consequently, since acoustic waves can be simultaneously detected in a plurality of places, there are effects such as a reduction in a detection time and suppression of the influence of a body movement. Acoustic impedance matching agent such as gel or water for suppressing reflection of acoustic wave may be used between the acoustic wave detector 1105 and the object.

The region where light is irradiated on the object (the irradiation region) and the acoustic wave detector 1105 may be movable. As a method of moving the irradiation region, there are, for example, a method of moving the irradiation region using a movable mirror and a method of mechanically moving the light source itself. The position control means 1106 for moving the position of the acoustic wave detector 1105 moves the acoustic wave detector using a motor on the basis of information of a position sensor. The control unit 1102 performs control of the irradiation region and the position of the acoustic wave detector 1105. If the irradiation region and the acoustic wave detector 1105 are moved in synchronization with each other, it is possible to detect a photoacoustic wave from a wide range.

Further, concerning information necessary for extracting region information having quantitativity with respect to the photographing region, the control unit 1102 generates, as a part of photoacoustic wave signal information, information such as a photographing position and a photographing region, optics for the object during photographing, and information concerning acoustic wave measurement.

A photographing apparatus receives an instruction of a photographing region from the user via the input unit 106 and acquires a photoacoustic wave signal necessary for the photographing region. The photographing region is a three-dimensional region designated every time target photographing is performed. The photographing region can be designated in a photographable region decided by the specifications of the photographing apparatus. As a method of designating a photographing region, for example, there is a method of inputting a coordinate of vertexes of a rectangular parallelepiped and a numerical formula. There is also a method in which the user designates a rectangular region on an image of the object and specifies a three-dimensional region to match the size in the depth direction of the object in the region. The image of the object is obtained if the object is photographed through a transparent holding plate. The photographing region does not always need to be a rectangular parallelepiped.

Procedures of specific processing in this embodiment are explained with reference to FIGS. 4 to 11.

Figure 4:
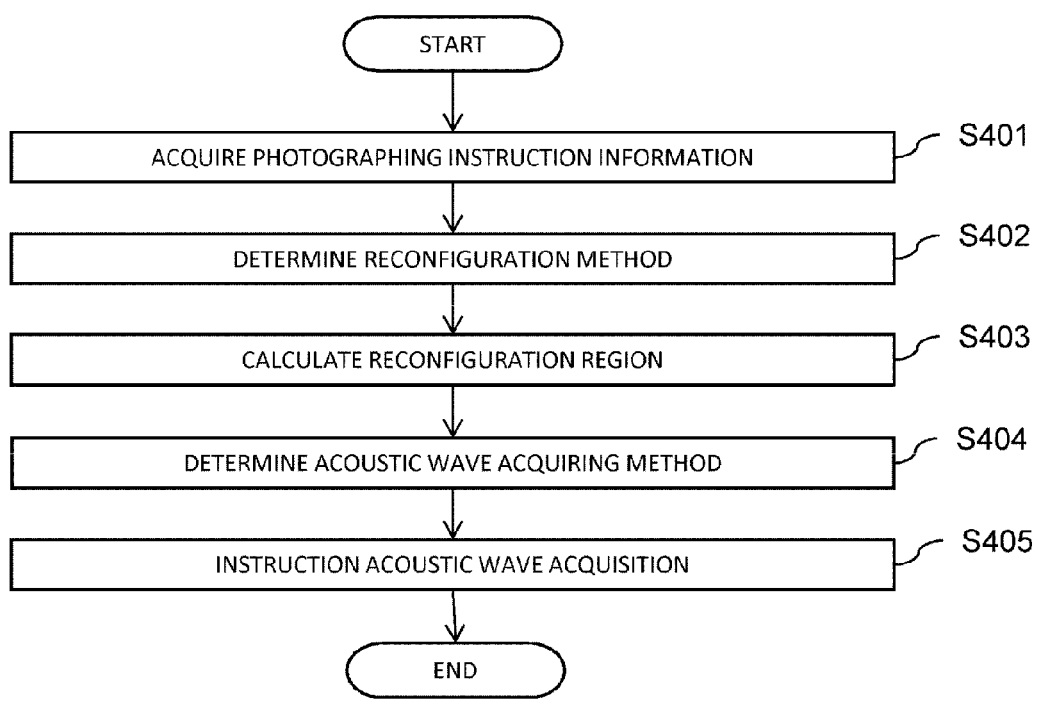
FIG. 4 is a flowchart for explaining a processing procedure from a photographing start to an acquisition instruction.

FIG. 4 is a flowchart for explaining a procedure in which, after an operation input for photographing by the user, the information processing unit 1000 determines a reconstruction method and a photoacoustic wave acquiring method and transmits the reconstruction method and the photoacoustic wave acquiring method to the photoacoustic wave signal measuring unit 1100. This flow is started at a point when, after setting an object (a breast of a subject, etc.) in close contact with the holding plate and fixing the object, a photographing technician sets parameters concerning photographing and desired image quality and performs operation for instructing a photographing start.

In step S401, the photographing instruction information acquiring unit 1001 acquires photographing instruction information such as photographing parameters concerning a photographing region and photoacoustic wave acquisition. When the photographing apparatus automatically sets an appropriate light irradiating method, an input from the user is unnecessary. In that case, necessary setting is performed according to output intensity of a laser, an angle of laser light, and the like.

The photographing instruction information acquiring unit 1001 transmits the acquired photographing instruction information to the reconstruction method determining unit 1002.

In step S402, the reconstruction method determining unit 1002 determines a reconstruction method on the basis of the photographing instruction information and information concerning photoacoustic wave signal measurement of the photoacoustic wave signal measuring unit 1100 stored in the main memory 102 or the magnetic disk 103 in advance.

The information concerning the photoacoustic wave signal measurement of the photoacoustic wave signal measuring unit 1100 is information concerning a photoacoustic wave signal measurement ability. For example, as information concerning a photographable region, there is information concerning the position and the size of a photographable region in the apparatus, a region where a probe can be scanned, and a region such as a range in which laser can be irradiated. Concerning irradiation light, information such as the number of rays of irradiation light, a wavelength, intensity (or a density distribution), an angle of irradiation light that can be controlled, moving speed of the probe, a signal processing ability of acoustic wave acquisition, and a laser irradiation interval is included.

When the photographing region included in the photographing instruction information is set as a reconstruction region, the reconstruction method determining unit 1002 determines a reconstruction method executable with designated image quality. As contents to be determined, there are, for example, an algorithm and parameters of the reconstruction processing, a correction method (e.g., light distribution correction) to be additionally carried out, and the like.

In step S403, the reconstruction method determining unit 1002 calculates a reconstruction region to be set as a target of the reconstruction processing during photographing. Usually, the photographing region is the reconstruction region. However, the photographing region and the reconstruction region may be different. For example, when the ability of the apparatus is insufficient with respect to the photographing image quality designated by the photographing instruction information and the conditions such as the algorithm and the parameters during reconstruction, the photographing region and the reconstruction region may be set different. For a reduction of reconstruction processing time, a region where it is evident that image quality is low may be excluded from the reconstruction region. The reconstruction method determining unit 1002 generates, as reconstruction region information, the information for specifying the reconstruction regions.

The reconstruction method determining unit 1002 transmits the determined reconstruction method information and reconstruction region information to the reconstruction processing unit 1006 and the photoacoustic wave measuring method determining unit 1003.

In step S404, the photoacoustic wave measuring method determining unit 1003 determines a control method for the photoacoustic wave signal measuring unit 1100 for acquiring an acoustic wave in the reception region. Specifically, the photoacoustic wave measuring method determining unit 1003 determines a control method for probe scanning and light irradiation and generates the control method as photoacoustic wave acquisition information. At this point, information such as a relative positional relation between the object 1107 sandwiched between holding plats 1110 and the optical device 1104 and the acoustic wave detector 1105 may be included in the photoacoustic wave acquisition information.

The photoacoustic wave measuring method determining unit 1003 transmits the photoacoustic wave acquisition information to the photoacoustic wave measuring method instructing unit 1004.

Figure 5:
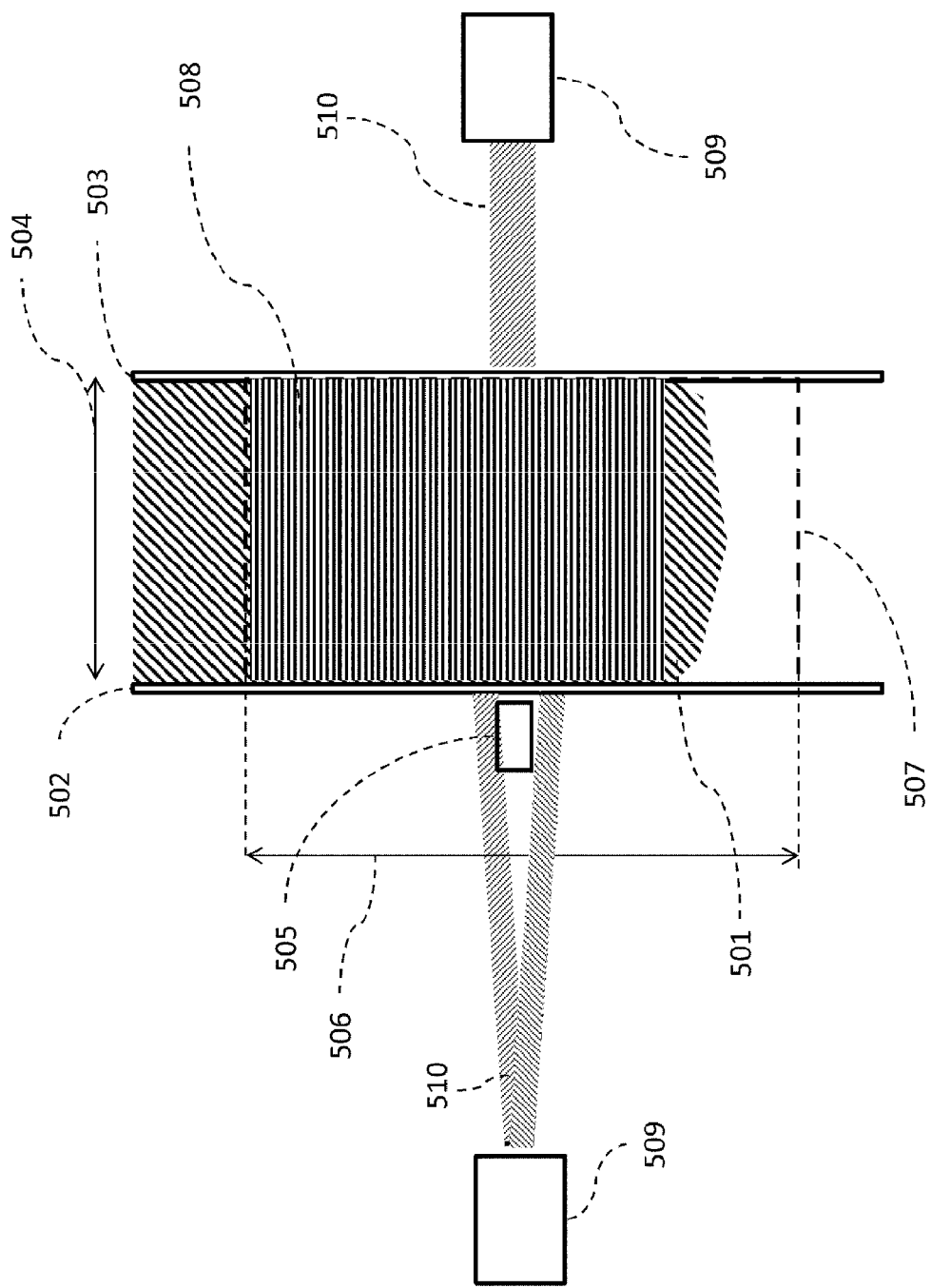
FIG. 5 is a diagram showing a relation between an object and a photographing region.

A relation between the photoacoustic wave acquisition information and the region having quantitativity is explained with reference to FIG. 5. In FIG. 5, an object 501 is sandwiched by two holding plates. A scanning surface 502 is the holding plate and is a surface on which a probe is scanned. A holding plate 503 is a plate that holds the object 501. The scanning surface 502 and the holding plate 503 transmit light and an acoustic wave. However, a part of the light and the acoustic wave is reflected on a boundary surface.

When the object 501 is a living organism such as a breast, there are a region where the object 501 is in close contact with the scanning surface 502 and a region where an air gap is present between the scanning surface 502 and the object 501. When the air gap is present in a route on which an acoustic wave reaches a probe 505 from the inside of the object, the acoustic wave cannot be received so well as in the case when the object and the holding plate are in close contact with each other. When the air gap is present in a route on which light is irradiated on the object, since an amount of light reaching respective segments of the object changes, quantitativity of photographing is spoiled. As a result, when an irradiation light amount becomes non-uniform, fluctuation occurs in a measurement result as well. Further, when a light absorption coefficient is calculated, attenuation of light in the object is sometimes estimated to correct a light amount distribution. However, when the air gap is present, reliability of an irradiation light amount, based on which the attenuation of the light is estimated, is deteriorated and quantitativity of estimation is spoiled. In this way, differences occurs in a sound pressure value, an absorption coefficient value, and the like according to presence or absence of the air gap.

When light is irradiated from both directions as shown in FIG. 5, a difference in a light amount reaching the inside of the object occurs between the close contact region and the region including the air gap because of the influence of light reflection on the object surface. As a result, in particular, when a light irradiation position is scanned, quantitativity becomes non-uniform.

The region having quantitativity in the photographing region means a region that can be treated as a region having similar quantitativity concerning photographing data in the photographing region set every time photographing of the photoacoustic diagnostic apparatus is performed. That is, the region having quantitativity treated in the present invention means a region where photographing data in the same photographing region can be treated at similar quantitativity, which is different from the quantitativity of the entire photographing region. For example, the quantitativity is not quantitativity concerning the entire photographing region unlike the case when aged deterioration occurs in the sensitivity of the probe and an output of the laser and the photoacoustic diagnostic apparatus provides photographing data with the aged deterioration corrected concerning the entire photographing region. For example, since a method of sandwiching the breast with the holding plates is different every time photographing is performed, a boundary line between the close contact region and the region including the air gap could also be different every time photographing is performed.

The information concerning the region having quantitativity in the photographing region, which is a target of the photographing function of the apparatus, means a region where light irradiation conditions and photoacoustic measurement conditions can be treated as equivalent conditions in photoacoustic wave measurement for the object in the photographing region. In this embodiment, the light irradiation conditions and the photoacoustic wave measurement conditions are the same in respective positions in a region surrounded by a region of the object that is in close contact with the holding plate. Therefore, the region is the region having quantitativity.

The holding plate 503 is used for fixing an object that is unstable in a shape and a position like a breast. When the holding plate 503 is used, since boundary surfaces between the object and the holding plates are planes, it is easy to calculate information concerning irradiation light such as light intensity. Reference numeral 504 denotes an interval of the holding plates. If the interval of the holding plates is fixed, the interval can be treated as a distance in the depth direction of the object. The shape and the size of the object, a three-dimensional position of the photographing region, and a region may be specified by other methods. For example, methods such as measurement of the shape and the size by a sensor an image processing from a camera image can be used.

The probe 505 is arranged in the acoustic wave detector 1105, moves in the scanning region on the scanning surface, and detects an acoustic wave. Reference numeral 506 denotes the height of the scanning region where the probe can move. This is equivalent to a region of the reception surface calculated by the photoacoustic wave measuring method determining unit 1003. The scanning region sometimes coincides with a boundary between the photographing region and the holding plate. However, the scanning region sometimes does not coincide with the boundary depending on setting of the photographing region and the scanning surface. A photographing region 507 indicated by a dotted line indicates a photographing range designated by the photographing instruction information. The photographing region can be arbitrarily set in the photographable range of the apparatus.

However, even in the photographing region, there is a region where the object 501 floats from the scanning surface 502 and the holding plate 503 depending on the shape and the size of the object. In the region, intensities of irradiation light and an acoustic wave cannot be quantitatively measured. A region obtained by excluding such a region where quantitative measurement cannot be performed from the photographing region is a region 508 having quantitativity.

An optical device 509 is a part of the optical device 1104 and irradiates irradiation light 510 on the object. Light is sometimes irradiated from the side of the probe as well as shown in FIG. 5. The control unit 1102 monitors the intensity of a detection signal of the acoustic wave detector 1105. When it is estimated that light directly reaches the acoustic wave detector 1105, the control unit 1102 does not use a signal of the light for image generation. The optical device 1104 may detect the close contact region between the object and the holding plate on the basis of a difference between reflected light of a close contact section and reflected light of a non-close contact section and set the close contact region as the irradiation region.

A state in which the object 501 is in close contact with the holding plate is explained with reference to FIGS. 6A and 6B. FIG. 6A is a diagram in which the object 501 is viewed from a side surface (an extending direction of the holding surface). It is seen that a region 601 where the object 501 is in close contact with the holding plate and a region where the object 501 floats from the holding plate are formed in the photographing region. FIG. 6B shows the object viewed from the scanning surface side. The close contact region and the region where the object 501 floats are also present. A region 602 surrounded by the region 601 where the object 501 is in close contact with the holding plate is the region having quantitativity in this embodiment.

Figure 7A:
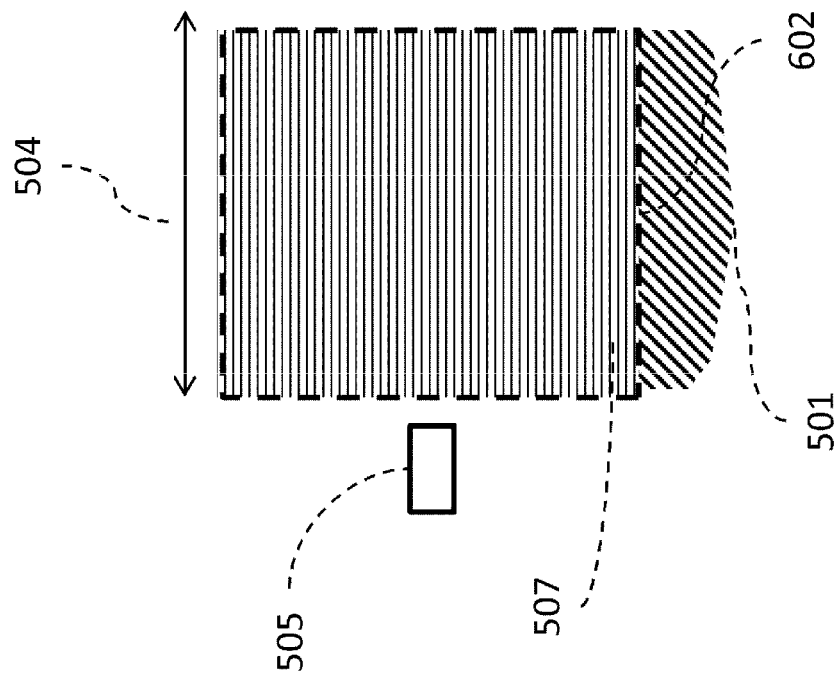
FIGS. 7A and 7B are diagrams showing a relation between a photographing region and a quantitative region, which coincide with each other.
Figure 7B:
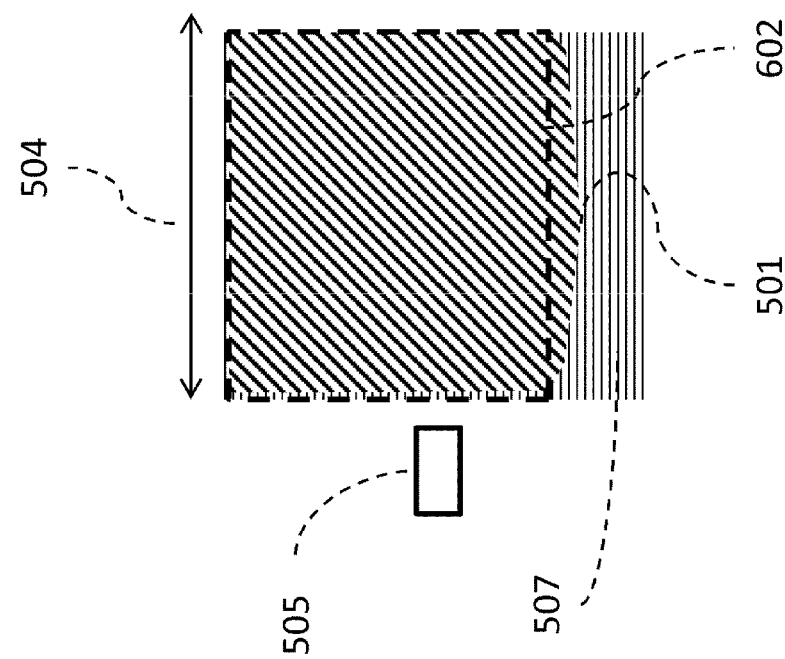

The entire photographing region that can be regarded as the region having quantitativity is explained with reference to FIGS. 7A and 7B. In FIG. 7A, the object 501 and a region other than the object 501 are present in the photographing region. When a living organism such as a breast is held by the holding plates, in order to photograph the vicinity of an end of the breast, it is necessary to photograph the photographing region in such a position. On the other hand, in FIG. 7B, the object occupies the entire photographing region. In this case, an entire region of a three-dimensional region reconstructed because the entire photographing region can be treated as the same conditions is the region having quantitativity.

In FIG. 5, an optical device may be arranged beside the probe 505 as well to control a light amount, an incident angle, and the like of irradiation light. Probes may be arranged on both the holding plates to acquire acoustic waves in a plurality of directions.

In step S405, the photoacoustic wave measuring method instructing unit 1004 generates photoacoustic wave acquisition instruction information on the basis of the photoacoustic wave acquisition information and transmits the photoacoustic wave acquisition instruction information to the photoacoustic wave signal measuring unit 1100. The photoacoustic wave acquisition instruction information is configured by, for example, a command for instructing the photoacoustic wave signal measuring unit 1100 to acquire an acoustic wave and a parameter group.

According to the procedure explained above, the information processing unit 1000 determines a reconstruction method and a photoacoustic wave acquiring method and transmits the reconstruction method and the photoacoustic wave acquiring method to the photoacoustic wave signal measuring unit 1100. The three-dimensional photographing region and the reconstruction region (usually coinciding with the photographing region) are not always rectangular parallelepipeds. A region is designated by a numerical formula using a boundary surface and a vertex or designated by a voxel group associated with a coordinate system of the photographing region.

Figure 8:
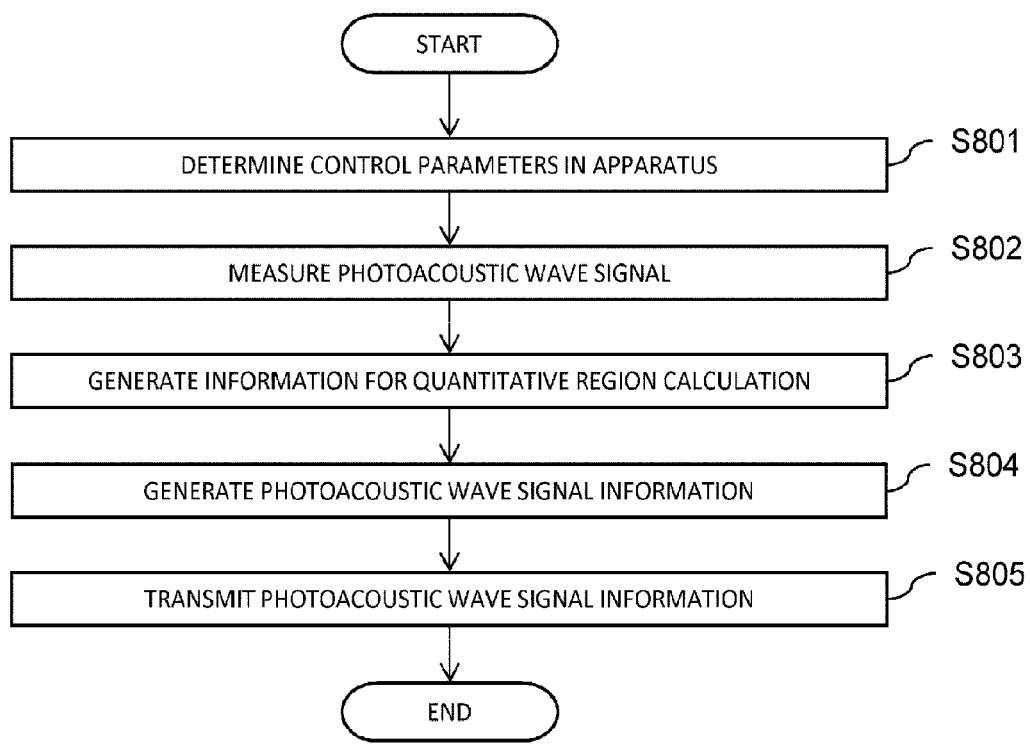
FIG. 8 is a flowchart for explaining a procedure of the photoacoustic wave signal measuring unit.

FIG. 8 is a flowchart for explaining a procedure in which the photoacoustic wave signal measuring unit 1100 carries out photoacoustic wave measurement concerning a designated photographing region, generates photoacoustic wave signal information, and transmits the photoacoustic wave signal information to the information processing unit 1000. Photographing is performed in the state shown in FIG. 5. This flow is started at a point when the photoacoustic wave signal measuring unit 1100 receives photoacoustic wave measurement instruction information.

In step S801, the photoacoustic wave signal measuring unit 1100 determines control parameters for controlling the optical device 1104 and the acoustic wave detector 1105. The control parameters concerning the optical device 1104 includes an irradiation position in the photographing region, the number of times of irradiation in the same position, irradiation timing, a wavelength, and intensity (or a density distribution). Concerning the acoustic wave detector 1105, the control parameters for detecting a photoacoustic wave such as the position of the probe and timing and time of photoacoustic wave measurement are determined. The control unit 1102 performs this processing on the basis of the photoacoustic wave measurement instruction information.

In step S802, the photoacoustic wave signal measuring unit 1100 measures an acoustic wave according to the determined control parameters.

In step S803, the photoacoustic wave signal measuring unit 1100 generates information used for a calculation of a region having quantitativity in the photographing region. In this embodiment, information concerning the irradiation region and the photoacoustic wave signal are equivalent to the information. The irradiation region is a region where the optical device 1104 irradiates light on the object 501 through the holding plate 503 during one photographing and is a region on a boundary surface between the object 501 and the holding plate 503.

The information concerning the light irradiation position and the irradiation region is converted into position information of a coordinate system of the photographing region. When the irradiation light is diffused light, the size of the irradiation region changes according to a distance from a light emission port to the boundary surface of the photographing region. For example, a condensing spot radius of a Gaussian beam is explained by Expression (8). When the distance from the light emission port changes, a relative distance between the boundary surface and a beam waist (a focal distance) changes. Therefore, the size of the irradiation region on the boundary surface of the photographing region also changes.

$$W = \lambda f / \pi W_0 \quad (8)$$

where W represents spot diameter, $W_0$ represents incident light radius, $\lambda$ represents wavelength, and f represents focal distance.

The size of the irradiation region can be measured from, for example, reflected light on the boundary surface of the photographing region. A value calculated from the specifications of the apparatus in advance may be used as a data table.

In the explanation in this embodiment, information concerning the region having quantitativity is generated after the photoacoustic wave measurement. However, information concerning the region having quantitativity may be generated for each light irradiation position. In this case, it is preferable to repeat the processing in steps S802 and S803 every time light irradiation is performed. It is also preferable to accurately measure, using a measuring apparatus such as an optical sensor as well, the intensity and an incident angle of the irradiation light reaching the boundary surface of the photographing region.

When the measurement of a photoacoustic wave ends, in step S804, the control unit 1102 generates photoacoustic wave signal information. At this point, information for calculating a region having quantitativity is also included in the photoacoustic wave signal information. The photoacoustic wave signal information is information concerning photoacoustic wave signals detected in respective positions on the scanning surface 502 during irradiation of light and information concerning irradiation light. The information concerning the photoacoustic wave signal includes photoacoustic wave acquisition conditions concerning photoacoustic wave signal detection and determination of a photoacoustic wave signal value.

In step S805, the photoacoustic wave signal measuring unit 1100 transmits photoacoustic wave signal information corresponding to the designated photographing region to the information processing unit 1000.

According to the procedure explained above, the photoacoustic wave signal measuring unit 1100 can transmit the photoacoustic wave signal information including the information for calculating a region having quantitativity to the information processing unit 1000.

Figure 9:
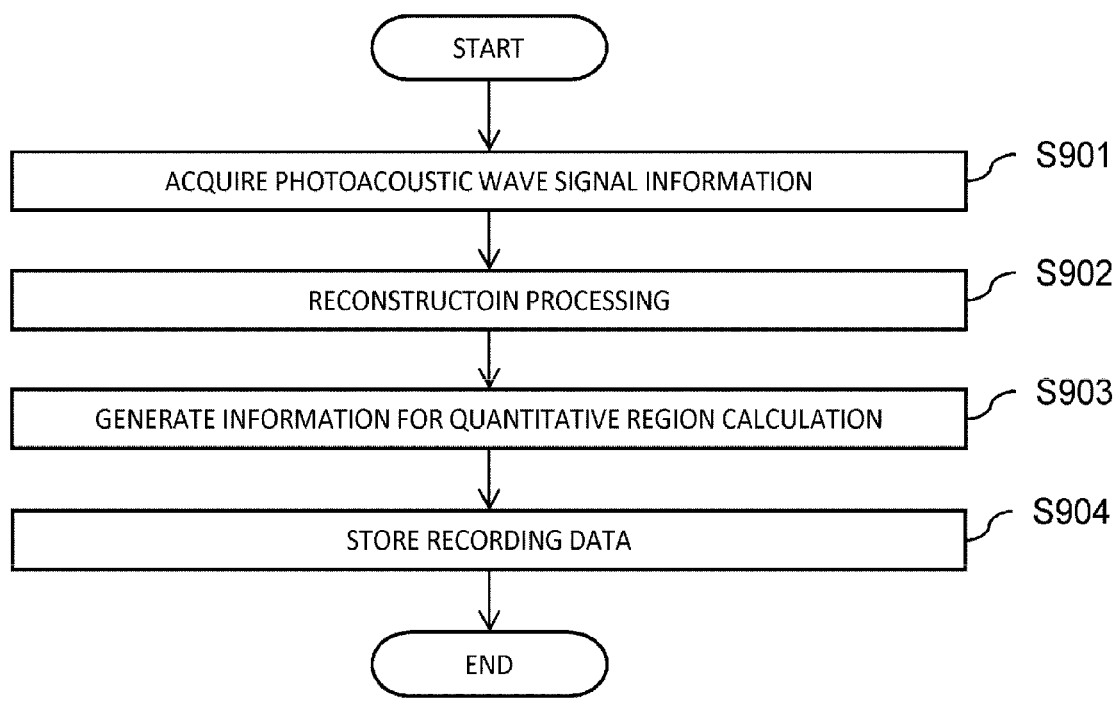
FIG. 9 is a flowchart for explaining a procedure in which the information processing unit extracts the quantitative region.

FIG. 9 is a flowchart for explaining a procedure in which the information processing unit 1000 carries out reconstruction processing on the basis of the transmitted photoacoustic wave signal information and stores recording data. This flow is started at a point when the photoacoustic wave signal information acquiring unit 1005 receives the photoacoustic wave signal information from the photoacoustic wave signal measuring unit 1100.

In step S901, the photoacoustic wave signal information acquiring unit 1005 acquires the photoacoustic wave signal information and transmits the photoacoustic wave signal information to the reconstruction processing unit 1006 and the quantitative region extracting unit 1007. The photoacoustic wave signal information acquiring unit 1005 may extract information for quantitative region calculation from the photoacoustic wave signal information and transmit the information for quantitative region calculation to the quantitative region extracting unit 1007. In this embodiment, the irradiation region is the information for quantitative region calculation.

In step S902, the reconstruction processing unit 1006, which acquires the photoacoustic wave signal information, performs reconstruction processing on the basis of the reconstruction method information and the reconstruction region information sent from the reconstruction method determining unit 1002 and generates reconstruction image data of the photographing region. The reconstruction image data is generated as, for example, volume data equivalent to the position and the size of the photographing region.

At this point, the reconstruction processing unit 1006 performs the reconstruction processing while determining superiority or inferiority of a signal value. A signal value obtained on the close contact region of the object and the scanning surface is detected in a normal range of an acoustic wave signal value from a living organism. However, in the non-close contact region, a signal value is extremely different because of the influence of a gap (a layer of the air). Therefore, it is possible to determine presence or absence of quantitativity of reconstructed images in the positions by sorting, with a method such as threshold processing, photoacoustic wave signals used in respective positions of a three-dimensional coordinate set as a target of the image reconstruction processing. Therefore, a reconstructed image in a position where the reconstructed image can be generated using an acoustic wave signal detected in a region on the scanning surface 502 of the acoustic wave detector is a region where acoustic wave measurement conditions can be regarded as equivalent.

The reconstruction processing unit 1006 transmits the generated reconstructed image to the quantitative region extracting unit 1007. In this embodiment, the reconstruction processing unit 1006 also transmits information concerning a region where acoustic wave measurement conditions can be regarded as equivalent in the reconstructed image region obtained by the threshold processing of the photoacoustic wave signal.

In step S903, the quantitative region extracting unit 1007 associates the reconstructed image data acquired from the reconstruction processing unit 1006 and the information for quantitative region calculation and generates information concerning a region having quantitativity concerning the reconstructed image. The quantitative region extracting unit 1007 regards the irradiation region as the close contact region of the irradiation region and the object and regards that light irradiation conditions of a region where the object overlaps a total of moved irradiation regions are equivalent.

Figure 10:
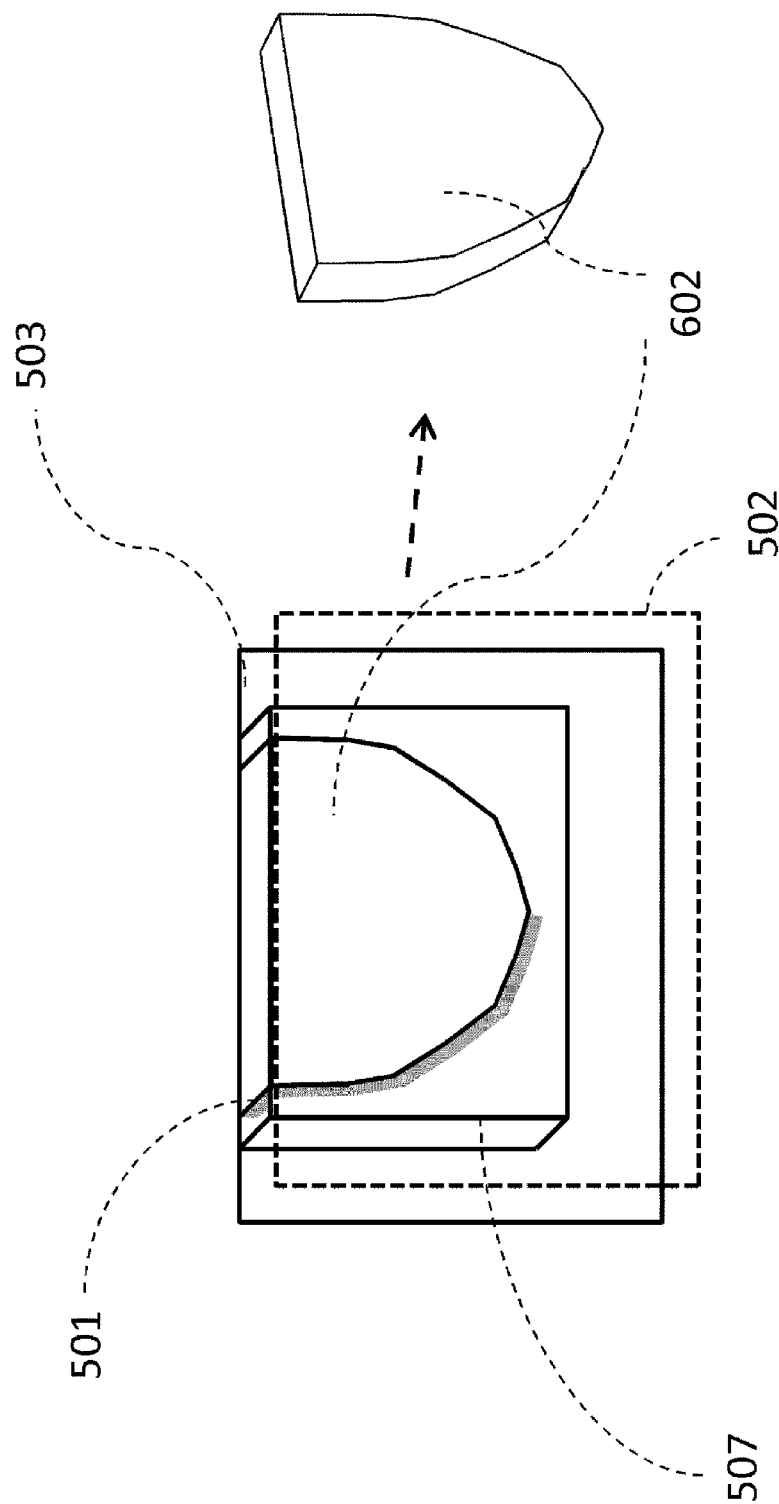
FIG. 10 is a diagram showing a relation between the photographing region and the quantitative region.

The quantitative region extracting unit 1007 extracts, as a region having quantitativity, a region where both of the acoustic wave measurement conditions and the light irradiation conditions are equivalent in the reconstructed image region. A relation between the object and the quantitative region in the photographing region is shown in FIG. 10. Information concerning the quantitative region is indicated by a group of dots associated with regions of the reconstructed image or a numerical formula. When recording data is generated as DICOM image data, information only has to be added by a method such as private tag.

The quantitative region extracting unit 1007 sends the reconstructed image data and information concerning a quantitative region with respect to the reconstructed image to the data recording unit 1008 as quantitative region information.

In step S904, the data recording unit 1008 stores the recording data.

Figure 11:
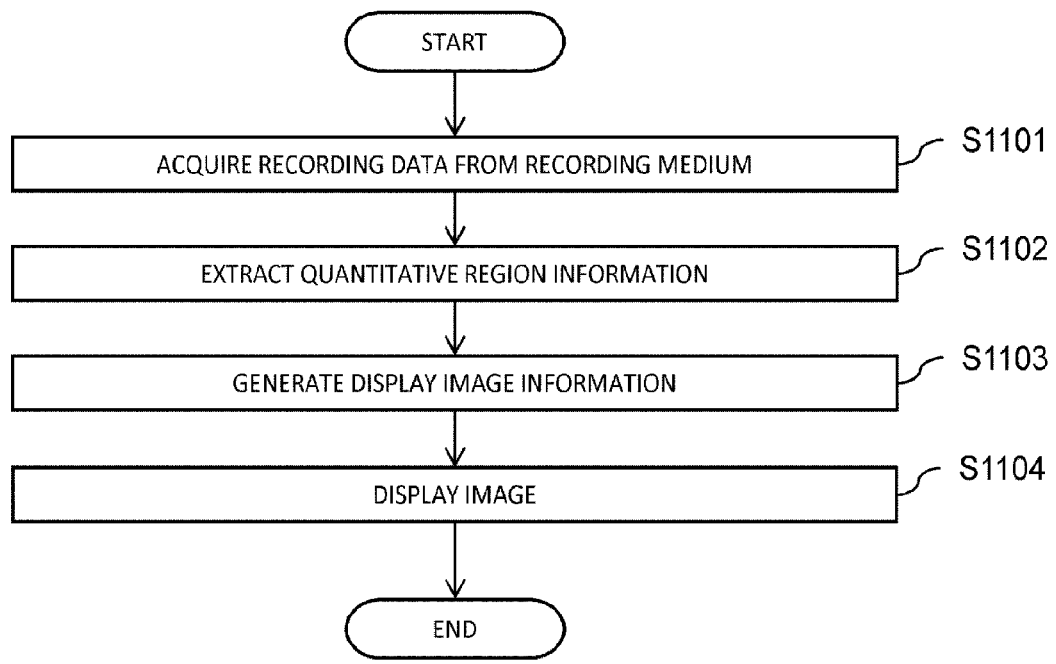
FIG. 11 is a flowchart for explaining a procedure of use of stored quantitative region information.

A procedure of displaying the reconstructed image using information concerning irradiation light stored in the recording data is explained with reference to a flowchart of FIG. 11. This flow is started at a point when the information processing unit 1000 starts to read the recording data.

In step S1101, the data acquiring unit 1009 in the information processing unit 1000 reads the recording data from the recording data file 1200 and transmits the recording data to the data analyzing unit 1010.

In step S1102, the data analyzing unit 1010 acquires the reconstructed image data and the quantitative region information with respect to the reconstructed image from the recording data and transmits the reconstructed image data and the quantitative region information to the display information generating unit 1011 together with information for identifying a type of information.

In step S1103, the display information generating unit 1011 generates display image information using the reconstructed image data. As a method of displaying the display image information, when the configured image is displayed in multi planner reconstruction (MRP), there is a method of superimposing and displaying a reconstructed sectional image and a boundary line indicating image quality on the sectional image. The display image may be displayed by volume rendering. Instead of the display image, information other than an image such explanation by text based on as pixel values in positions of a three-dimensional reconstructed image, that is, voxel values of volume data may be generated.

The display information generating unit 1011 may generate arbitrary display information related to the reconstructed image. For example, if only the boundary surface of the quantitative region is displayed in a color different from a color of the other boundary surfaces, it is easy to identify the boundary surface. It is also possible to generate display image information added with graphic for easily identifying a boundary line or a plane.

It is also possible to identify a type of information and properly use, according to the quantitative region information, for example, graphic added to a display image by volume rendering of the reconstructed image. The color or the graphic representation may be changed according to the display size, the direction, or the like of the region. Quantitativity may be classified by colors according to stages or degrees of quantitativity may be indicated by numerical values, graphs, color bars, or the like.

Further, when a function image in which the shape of the object cannot be displayed such as a light absorption coefficient or an oxygen saturation value is displayed, it is effective to generate and display a quantitative region. In particular, a value of an oxygen saturation image is also calculated in a region where the object is absent. Therefore, it is possible to assist a diagnosis by displaying the quantitative region information.

The display information generating unit 1011 transmits the generated display information to the display unit 1012.

In step S1104, the display unit 1012, which is the display device such as the monitor 105, displays the display information generated by the display information generating unit 1011.

According to the procedure, it is possible to display the reconstructed image using the quantitative region information stored in the recording data.

In the example explained in this embodiment, the photoacoustic wave signal measuring unit 1100 generates the information for quantitative region calculation with respect to the photographing region and the information processing unit 1000 generates the quantitative region information with respect to the reconstructed image. However, the photoacoustic wave signal measuring unit 1100 may generate the quantitative region information. The information processing unit 1000, to which information of the apparatus concerning the information for quantitative region calculation is transmitted, may generate the information for quantitative region calculation.

The photoacoustic wave measuring method determining unit 1003 may be included in the photoacoustic wave signal measuring unit 1100. In this case, the photoacoustic wave measuring method instructing unit 1004 transmits the reconstruction method information and the reconstruction region information to the photoacoustic wave signal measuring unit 1100. The processing concerning calculation of a reception region is executed in the photoacoustic wave signal measuring unit 1100.

Further, a method of carrying out the processing in a photographing apparatus in which the information processing unit 1000 and the photoacoustic wave signal measuring unit 1100 are integrated may be adopted. An embodiment in which the information processing unit 1000 including only the data acquiring unit 1009, the data analyzing unit 1010, the display information generating unit 1011, and the display unit 1012 uses the recording data file 1200 is also included in the embodiments of the present invention.

In the example explained in this embodiment, the reconstructed image after storage is displayed. However, the reconstructed image and the quantitative region information may be directly transmitted to the display information generating unit and displayed without storing the reconstructed image.

By carrying out the procedure explained above, it is possible to realize the photoacoustic diagnostic apparatus of the present invention. By carrying out the present invention according to the procedure, it is possible to store and display photographing data of the photoacoustic diagnostic apparatus and analysis data such as an oxygen saturation value in association with a region having quantitativity during photographing.

Second Embodiment

A second embodiment is a configuration in which a camera configured to photograph the close contact region of the holding plate and the object is added to the configuration of the first embodiment. In this case, the holding plate has a certain degree of transparency.

In the generation of information for quantitative region calculation in step S803, the object 501 is photographed by the camera through the holding plate. At least two places, i.e., the scanning surface 502, the photographing region of which is included in an image, and the holding plate 503 are photographed. The positions and the postures of the holding plate and the object in the image are associated with coordinates of the photographing region and set as the information for quantitative region calculation. Timing of the photographing by the camera may be points of time designated by the user such as before and after the photoacoustic wave signal measurement in step S802.

In step S902, the reconstruction processing unit 1006 is different from the first embodiment in that the reconstruction processing unit 1006 executes normal reconstruction processing.

Further, in step S903, the quantitative region extracting unit 1007 extracts the close contact region from a camera image on the side of the scanning surface 502. As in the first embodiment, the quantitative region extracting unit 1007 calculates a region where acoustic wave measurement conditions can be regarded as equivalent in the reconstructed image region. A method of extracting the close contact region only has to be general region extraction or edge extraction processing in an image. To accurately extract a region, an image in the apparatus in a state in which the object is not held is prepared in advance and extraction target regions are narrowed down using a difference image of the image. Alternatively, processing such as skin color extraction can also be concurrently used. The quantitative region extracting unit 1007 also extracts a region from an image obtained by photographing the object from the side of the holding plate 503 on the projection side, calculates a region where light irradiation conditions can be regarded as equivalent, and generates quantitative region information.

The procedure other than the steps explained above is the same as the procedure in the first embodiment. With the processing procedure in this embodiment, a further effect is obtained that calculation of a quantitative region is accurately performed by a photographed camera image.

Third Embodiment

In a third embodiment, transmission and reception of an ultrasound wave signal is performed simultaneously with photoacoustic wave photographing and information concerning a region where an object is in close contact with a holding plate is obtained to extract a quantitative region.

A probe in this embodiment can take a configuration explained below. First, a probe for ultrasound wave transmission and reception is arranged, only reception of an acoustic wave is performed in measurement of a photoacoustic wave, and both transmission and reception are performed in acoustic wave measurement by transmission and reception of an ultrasound wave. A configuration in which a probe for a photoacoustic wave and a probe for ultrasound wave transmission and reception are separately arranged is also possible. With these configurations, it is possible to measure two kinds of acoustic wave signals in the same photographing region during one photographing. It is possible to use both photoacoustic wave measurement and echo wave measurement according to timing control for light irradiation and ultrasound transmission and reception.

In this embodiment, the photoacoustic wave measurement and the ultrasound wave transmission and reception are separately performed in one photographing processing to generate a photoacoustic wave image and a three-dimensional ultrasound wave image. A close contact region of the object and the holding plate is extracted using the three-dimensional ultrasound wave image and a quantitative region is further extracted.

In the flow, measurement of an ultrasound wave signal by transmission and reception of the ultrasound wave signal is also executed within the same photographing time as the photoacoustic wave signal measurement in step S802.

In the generation of information for quantitative region calculation in step S803, acoustic wave measurement of an ultrasound wave is performed in addition to the measurement of a photoacoustic wave signal. The control unit 1102 controls a probe for ultrasound wave measurement. That is, as in the scanning during the photoacoustic wave measurement, the control unit 1102 scans the acoustic wave detector 1105 and transmits and receives an ultrasound wave. In the scanning control of the acoustic wave detector 1105, the photoacoustic wave measurement and the ultrasound wave transmission and reception may be repeated for each position. After one of the measurements, the same position may be scanned again to perform the other measurement. The control unit 1102 generates, from a result of ultrasound wave transmission and reception, a three-dimensional ultrasound wave image including an ultrasound wave image near a boundary of the object 501, the scanning surface 502, and the holding plate 503.

Like the photoacoustic wave image, the three-dimensional ultrasound wave image can also be generated as volume data. In that case, the photographing region is divided into voxels at the same pitch and necessary interpolation processing or the like is performed in the voxels. By generating such volume data of the three-dimensional ultrasound wave image, data having high consistency with a region of a three-dimensional image based on a photoacoustic wave is obtained.

The control unit 1102 extracts, from the three-dimensional ultrasound wave image, a sectional image in which the object 501 corresponds to the boundary between the scanning surface 502 and the holding plate 503. As in the case of the camera image, the control unit 1102 generates information for quantitative region calculation.

In step S902, the reconstruction processing unit 1006 executes normal reconstruction processing.

Further, in step S903, the quantitative region extracting unit 1007 extracts a region of a close contact section of the object from an ultrasound wave sectional image indicating a state of the object 501 that is in close contact with the scanning surface 502. The quantitative region extracting unit 1007 calculates a region where acoustic wave measurement conditions can be regarded as equivalent in the reconstructed image region. The quantitative region extracting unit 1007 extracts the region of the close contact section of the object from an ultrasound wave sectional image indicating a state of the object 501 that is in close contact with the holding plate 503 on the light projection side, calculates a region where light irradiation conditions can be regarded as equivalent, and generates quantitative region information.

The procedure other than the steps explained above is the same as the procedure in the first embodiment. According to this embodiment, it is possible to accurately perform region extraction on the basis of a difference in acoustic impedance according to ultrasound wave measurement. Therefore, it is possible to perform highly accurate measurement.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-005534, filed on Jan. 16, 2012, which is hereby incorporated by reference herein in its entirety.

What is claimed is:

1. An object information acquiring apparatus comprising:
   a holding unit configured to hold an object;
   a detector configured to output a signal by detecting a photoacoustic wave generated from the object held by the holding unit and irradiated with light from a light source, said detector having a reception region, and said reception region being disposed in contact with said holding unit;
   a generator configured to generate, using the signal, image data indicating characteristic information about at least a portion in the object;
   a region acquirer configured to acquire information on a region in the image where said holding unit contacts the object; and
   a display information acquirer configured to cause a display unit to display display information corresponding to the image data and display information corresponding to the information on the region.

2. The object information acquiring apparatus according to claim 1, wherein
   first light having a first wavelength and second light having a second wavelength are irradiated from the light source, and
   said generator is configured to generate oxygen saturation as the characteristic information by using measurement values of photoacoustic waves respectively corresponding to the first light and the second light.

3. The object information acquiring apparatus according to claim 1, wherein said generator is configured to generate oxygen saturation distribution as the image data.

4. The object information acquiring apparatus according to claim 1, further comprising a recording unit configured to record the information on the region in association with the image data.

5. The object information acquiring apparatus according to claim 4, wherein said recording unit is configured to record the image data as DICOM image data and the information on the region as a private tag in association with the DICOM image data.

6. The object information acquiring apparatus according to claim 1, further comprising an input unit configured to input a photographing region,
wherein said generator is configured to generate the image data in the photographing region.

7. The object information acquiring apparatus according to claim 1, wherein said display information acquirer is configured to cause the display unit to display the display information corresponding to the information on the region such that the region in the image data where said holding unit contacts the object and a region in the image data where said holding unit does not contact the object are distinguishable.

8. The object information acquiring apparatus according to claim 1, wherein the display information corresponding to the information on the region is a boundary line that enables identification of the region in the image data where said holding unit contacts the object.

9. The object information acquiring apparatus according to claim 1, wherein said display information acquirer is configured to cause the display unit to display the region in the image data where said holding unit contacts with object and a region in the image data where said holding unit does not contact the object in different colors.

10. The object information acquiring apparatus according to claim 1, wherein
said holding unit includes two plates which sandwich the object, and
said region acquirer is configured to acquire three-dimensional regions between a region where one of said plates and the object are in contact and a region where the other of said plates and the object are in contact as the information on the region.

11. The object information acquiring apparatus according to claim 1, wherein
said holding unit includes two plates which sandwich the object, and
said region acquirer is configured to acquire a overlapped region as the information on the region, the overlapped region being a region where a first three-dimensional region and a second three dimensional region overlap each other, the first three-dimensional region being a region between a region where one of said plates and the object are in contact and the other of said plates, and the second three-dimensional region being a region between a region on said one of said plates where the light is irradiated and said other of said plates.

12. The object information acquiring apparatus according to claim 1, wherein said region acquirer is configured to acquire the region in the image data where said holding unit contacts the object using the signal.

13. The object information acquiring apparatus according to claim 1, further comprising a camera configured to photograph the object,
wherein said region acquirer is configured to acquire the information on the region using an image photographed by said camera.

14. The object information acquiring apparatus according to claim 1, further comprising an ultrasound probe configured to transmit an ultrasound wave to the object and receive an echo wave of the ultrasound wave to output an ultrasound signal,
wherein said region acquirer is configured to acquire the information on the region using the ultrasound signal.

15. The object information acquiring apparatus according to claim 14, wherein said ultrasound probe is configured to receive the echo wave from a portion on the object where said detector detects the photoacoustic wave.

16. The object information acquiring apparatus according to claim 1, wherein said detector is movable and is configured to move and detect the photoacoustic wave from a plurality of portions of the object.

17. The object information acquiring apparatus according to claim 1, wherein the reception region of said detector is disposed in contact with said holding unit via an acoustic matching agent.

18. A method of displaying information on an object, comprising the steps of:
outputting a signal by detecting, with a detector, a photoacoustic wave generated from an object, the object being held with a holding unit, the object being irradiated with light from a light source, a reception region of the detector being disposed in contact with the holding unit;
generating, using the signal, image data indicating characteristic information in the object;
acquiring information on a region in the image where the holding unit contacts the object; and
displaying display information corresponding to the image data and display information corresponding to the information on the region.

19. A non-transitory computer readable medium storing a program causing a computer to execute a process comprising the steps of:
outputting a signal by detecting, with a detector, a photoacoustic wave generated from an object, the object being held with a holding unit, the object being irradiated with light from a light source, a reception region of the detector being disposed in contact with the holding unit;
generating, using the signal, image data indicating characteristic information in the object;
acquiring information on a region in the image where the holding unit contacts the object; and
displaying display information corresponding to the image data and display information corresponding to the information on the region.

* * * * *